US010154695B2

(12) United States Patent
Jin (10) Patent No.: US 10,154,695 B2
(45) Date of Patent: Dec. 18, 2018

(54) PERSONAL WEARABLE AIRBAG DEVICE FOR PREVENTING INJURY

(71) Applicant: Xin Jin, Waterloo (CA)

(72) Inventor: Xin Jin, Waterloo (CA)

( * ) Notice: Subject to any disclaimer, the term of this patent is extended or adjusted under 35 U.S.C. 154(b) by 132 days.

(21) Appl. No.: 14/980,001

(22) Filed: Dec. 28, 2015

(65) Prior Publication Data

US 2017/0181485 A1  Jun. 29, 2017

(51) Int. Cl.
| | | |
|---|---|---|
| *A41D 13/018* | (2006.01) | |
| *A61B 5/11* | (2006.01) | |
| *A41D 1/00* | (2018.01) | |
| *A41F 9/00* | (2006.01) | |

(52) U.S. Cl.
CPC .......... *A41D 13/018* (2013.01); *A41D 1/002* (2013.01); *A41F 9/002* (2013.01); *A61B 5/1117* (2013.01)

(58) Field of Classification Search
CPC ............................. A41D 13/018; A61B 5/1117
See application file for complete search history.

(56) References Cited

U.S. PATENT DOCUMENTS

| | | | | | |
|---|---|---|---|---|---|
| 4,977,623 A | * | 12/1990 | DeMarco | ............. | A41D 13/018 2/456 |
| 5,362,098 A | * | 11/1994 | Guill | .................... | A41D 13/018 2/456 |
| 5,500,952 A | * | 3/1996 | Keyes | .................. | A41D 13/018 2/465 |
| 5,937,443 A | * | 8/1999 | Kageyama | ........... | A41D 13/018 2/455 |
| 2003/0182040 A1 | * | 9/2003 | Davidson | ............. | A41D 13/018 701/45 |
| 2004/0003455 A1 | * | 1/2004 | Davidson | ............. | A41D 13/018 2/455 |
| 2004/0111790 A1 | * | 6/2004 | Dainese | ............... | A41D 13/018 2/456 |
| 2004/0183283 A1 | * | 9/2004 | Buckman | ............. | A41D 13/018 280/730.1 |
| 2005/0067816 A1 | * | 3/2005 | Buckman | ............. | A41D 13/018 280/730.1 |
| 2006/0212986 A1 | * | 9/2006 | Mahoney | ............. | A41D 13/018 2/69 |
| 2006/0267779 A1 | * | 11/2006 | Ishikawa | ............... | A41D 13/018 340/573.1 |
| 2006/0288464 A1 | * | 12/2006 | Warden | ................ | A41D 13/018 2/69 |
| 2008/0001735 A1 | * | 1/2008 | Tran | .................... | G06F 19/3418 340/539.22 |
| 2009/0254003 A1 | * | 10/2009 | Buckman | ............... | A61B 5/1117 600/595 |
| 2010/0004567 A1 | * | 1/2010 | Ishikawa | ............... | A41D 13/018 600/595 |
| 2012/0131718 A1 | * | 5/2012 | Uchida | .................. | A62B 99/00 2/69 |
| 2013/0326800 A1 | * | 12/2013 | Kim | ..................... | A41D 13/018 2/455 |

(Continued)

*Primary Examiner* — Ruth Ilan (57) ABSTRACT

For people with reduced physical ability such as elderly people, risks of bodily injuries are high. Once an injury occurs, a victim suffers, sometimes a victim even may not survive. To help such people, a personal wearable device without adding much inconvenience in normal life is disclosed. This personal wearable device is able to detect dangerous conditions and automatically deploy airbags when needed to prevent or mitigate potential bodily injuries.

17 Claims, 6 Drawing Sheets

(56) References Cited

U.S. PATENT DOCUMENTS

| | | | |
|---|---|---|---|
| 2014/0047623 A1* | 2/2014 | Richards | A41D 13/018 2/455 |
| 2014/0123374 A1* | 5/2014 | Gelston | A41D 13/018 2/455 |
| 2015/0101112 A1* | 4/2015 | Balbien | A41D 13/018 2/465 |
| 2015/0120007 A1* | 4/2015 | Guez | G05B 13/0205 700/47 |
| 2015/0272248 A1* | 10/2015 | Briggs | A41F 9/002 2/465 |
| 2016/0174626 A1* | 6/2016 | Mazzarolo | A41D 13/018 2/455 |
| 2016/0183607 A1* | 6/2016 | Lopez Yunez | A41D 13/018 2/455 |
| 2017/0006931 A1* | 1/2017 | Guez | A61B 5/0476 2/455 |
| 2017/0143055 A1* | 5/2017 | Duncan | A41D 13/018 |
| 2017/0208874 A1* | 7/2017 | Davenport | A41D 13/018 |
| 2017/0224031 A1* | 8/2017 | Raanan | A41D 13/018 |
| 2017/0277158 A1* | 9/2017 | Hyde | G05B 19/0428 |
| 2017/0281056 A1* | 10/2017 | Raanan | A61L 35/1117 |

* cited by examiner

PERSONAL WEARABLE AIRBAG DEVICE FOR PREVENTING INJURY

CROSS-REFERENCE TO RELATED APPLICATION

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING

Not Applicable.

BACKGROUND OF THE INVENTION

Field of the Invention

This invention relates generally to wearable device to prevent bodily injury, in particular, to an airbag device and its control method to prevent bodily injury caused by impacts such as falling down, or being hit by high speed blunt objects.

Description of the Related Art

Airbags have been widely used in automobiles to prevent injury in vehicle collision accidents. An airbag inflates when a collision is detected by a control unit through various sensors installed on vehicle (e.g., accelerometers, impact sensors, side door pressure sensors, wheel speed sensors, gyroscopes, brake pressure sensors, and seat occupancy sensors), creating a cushion between a driver/passenger and other hard objects on the vehicle, reducing the risk of severe bodily injury.

Wearable devices such as helmets, armors, bulletproof vests, and kneepads may be used to protect particular parts of body from injury when a person is performing specific tasks. Particular groups of people such as elderly people, handicapped persons, construction site workers experience higher risks of bodily injury than many others, on the other hand, wearing armors and helmets all time is inconvenient for them. There is a need in the art to smartly deploy a protection against injury when needed while minimizing the inconvenience caused by wearable protection devices.

BRIEF SUMMARY OF THE INVENTION

In one aspect, the invention provides an airbag device wearable on a user body for preventing bodily injury of the user, comprising: at least one inflatable airbag, mounted on the airbag device for absorbing energy when an object hits the body of the user; at least one airbag inflator, for accepting an igniting signal to inflate the at least one inflatable airbag; at least one radar based on detecting ultrasound signals reflected by surrounding objects, for detecting dangerous objects that may hit the body of the user; and a controller, coupled with the at least one airbag inflator and the at least one radar, for receiving information from devices that are coupled with, making decisions of airbag inflation, sending igniting signal to the at least one airbag inflator, and controlling the airbag device.

In another aspect, at least one embodiment of the invention provides an airbag device wearable on a user body for preventing bodily injury of the user, wherein a controller of the airbag device is operable to determine whether or not to inflate at least one airbag based, at least in part, on a detected relative velocity and a distance of an object to the user, as reported by at least one radar that is based on Doppler effects of reflected ultrasound signals from the object.

In yet another aspect, the invention provides a system for determining relative positions of segments of a body, comprising: a transmitter for transmitting a signal with a first time mark; a plurality of transponders placed at a plurality of distinct and predetermined positions on the segments of the body, for echoing an second time mark using an ultrasound signal with a predetermined delay relative to the first time mark received by the individual transponders; at least three ultrasound receivers placed at distinct positions that are fixed relative to one another, for receiving the second time marks echoed by each of the transponders, and measuring propagation delays thereof; a processor, coupled with the transmitter and the receivers, for determining the relative positions of segments of body; and whereby, the system is operable to determine the relative positions of segments of the body, through computing positions of the transponders based on trilateration of distances calculated through a known ultrasound propagation speed, and the measured propagation delays of the second time marks.

Other aspects of the invention will become clear thereafter in the detailed description of the preferred embodiments and the claims.

BRIEF DESCRIPTION OF THE DRAWINGS

For a better understanding of the invention and to show more clearly how it may be carried into effect, reference will now be made, by way of example only, to the accompanying drawings which show at least one exemplary embodiment of the invention and in which.

DETAILED DESCRIPTION OF THE INVENTION

It will be appreciated that in the description herein, numerous specific details are set forth in order to provide a thorough understanding of the invention. However, it will be understood by those of ordinary skill in the art that the invention may be practiced without these specific details. In other instances, well-known methods, procedures and components have not been described in detail so as not to obscure the invention. Furthermore, this description is not to be considered as limiting the scope of the invention, but rather as merely providing a particular preferred working embodiment thereof.

Figure 1:
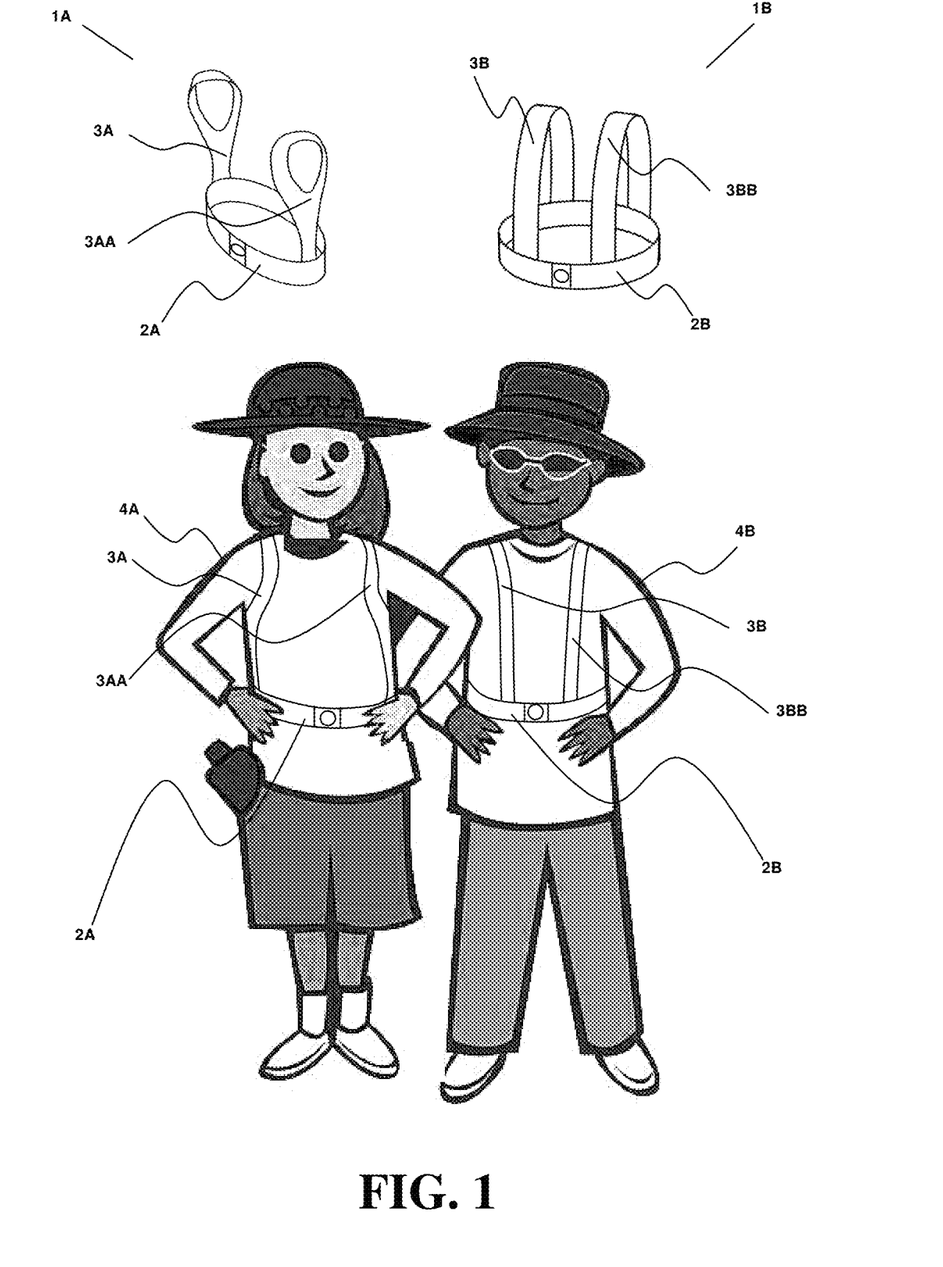
FIG. 1 illustrates a physical look of two exemplary embodiments of wearable airbag devices, when the airbag is not inflated.

FIG. 1 illustrates a physical look of two exemplary embodiments of wearable airbag devices, when the airbag is not inflated. In the embodiments, the airbag device 1A, 1B comprises a waist belt 2A, 2B and shoulder belts 3A, 3AA, 3B, 3BB. In the figure, use cases that users 4A, 4B wear the airbag devices are also illustrated. The shoulder belts 3A, 3AA, 3B, 3BB firmly connect the waist belt 2A, 2B, as shown. Preferably the belts are semi-flexible and durable, with adjustable length to fit a user body, and adapted to the shape of the body. Components of the airbag devices (to be described hereinafter) are embedded into the waist belt 2A, 2B and/or shoulder belts 3A, 3AA, 3B, 3BB. The device is preferably self contained and wearable on the upper body outside other clothing, and is suitable for all season use.

Figure 2:
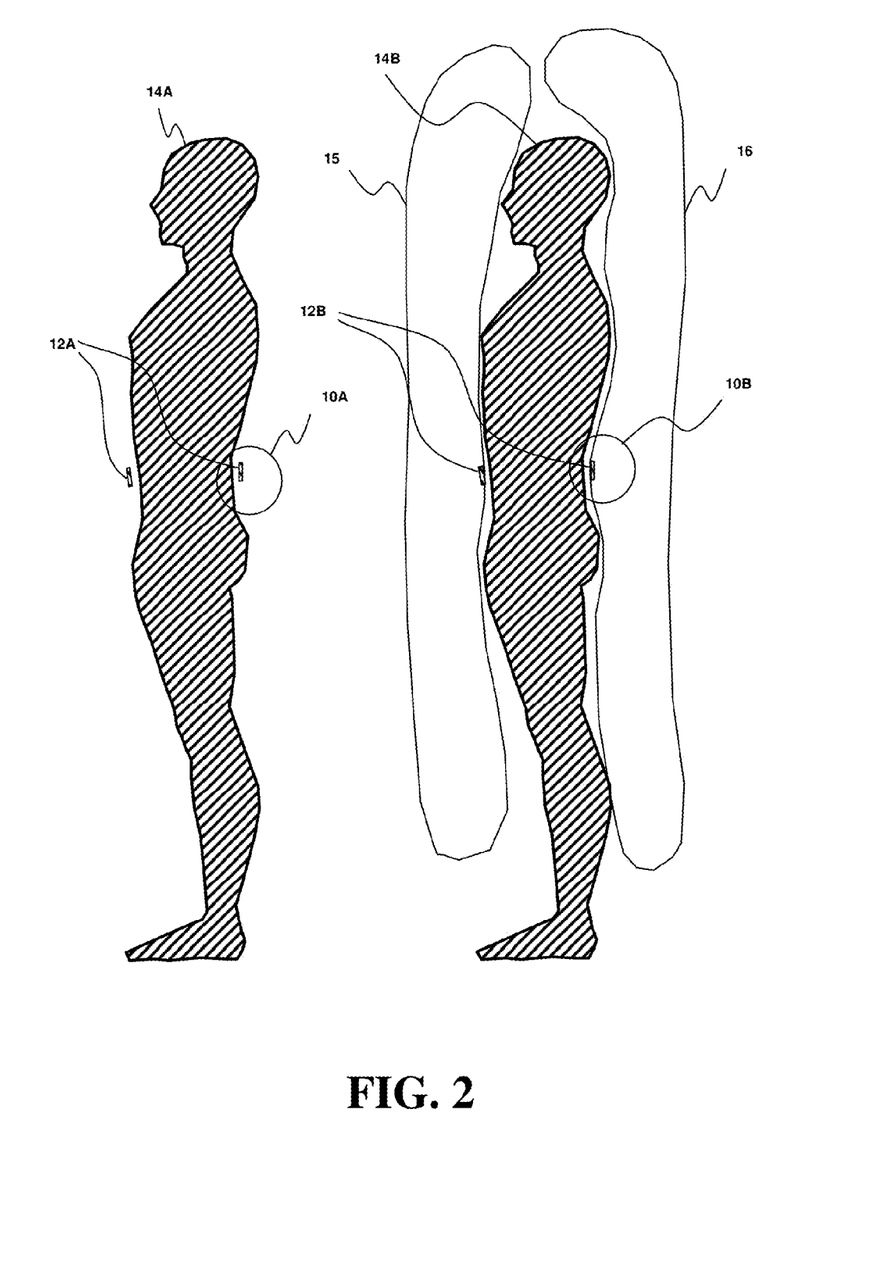
FIG. 2 illustrates sectional views of an exemplary embodiment of wearable airbag device before and after inflation.

FIG. 2 illustrates sectional views of the exemplary embodiment of wearable airbag device before and after inflation. Before inflating, the airbag device 12A is worn on user 14A outside regular clothing (not shown) of the user 14A (note that in the particular sectional view, only the waist belt 12A of the airbag device is shown). The device 12A is a merely a minor add-on accessory that the user 14A wears with minimal inconvenience to the user. When needed, at least one airbags 15, 16 are inflated from the airbag device 12B to protect various parts of the user body 14B. In the example of the embodiment in FIG. 2, one front airbag 15 and one rear airbag 16 are inflated to protect front and rear sides of the user body, respectively. Detailed views of 10A and 10B portions will be described hereinafter in FIG. 3.

Airbag inflation is a very rapid process that generates large amount of gas through, for example, chemical reactions of propellants. Before inflation the airbags are folded in small size and packed, for example, on the wearable belts. The container of propellants may be mounted on the outer side of the belts and wrapped inside the packed airbag. When inflation is initiated, an impact force may be applied backward on the belt. To reduce the pressure and pressure density toward the user body, the belt needs to be built with semi-flexible, durable and thermal resistant material that would distribute the pressure evenly through the inner surface of the belt to the user body without excessive temperature increase on its inner surface. To further reduce the impact under the belt towards user body, a few techniques can be used as will be discussed next.

Figure 3:
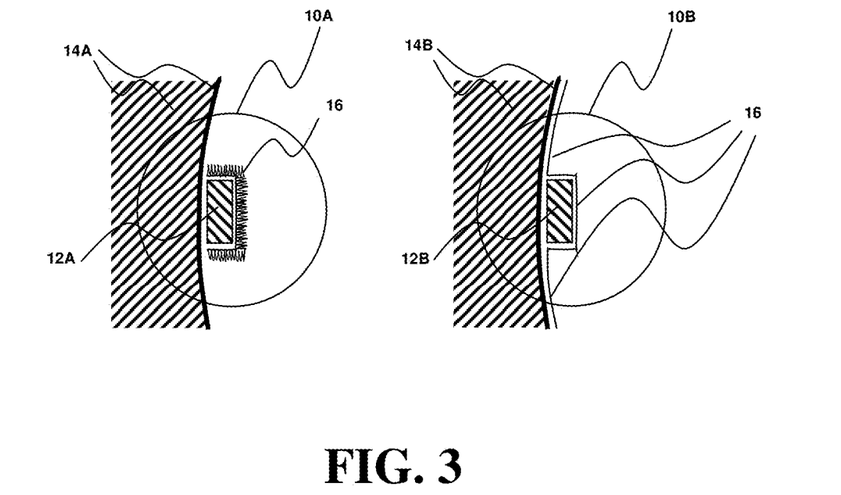
FIG. 3 shows detailed views of 10A and 10B portions of FIG. 2 in a preferred embodiment.

FIG. 3 shows detailed views of 10A and 10B portions of FIG. 2 in a preferred embodiment. When the airbag is not inflated 10A, the airbag 16 is folded around the belt 12A, ready to be inflated, as shown in FIG. 3 10A (not shown in FIG. 2 due to drawing scale). During and after inflation 10B, the airbag 16 preferably deploys and maintains a flat shape with the belt 12B on the user body side, adapted to the surface shape of the body 14B, so that pressure would evenly distributed to the body 14B under both the belt 12B and the bag 16, rather than creating excessively stronger impact under the area of the belt 12B.

Figure 4:
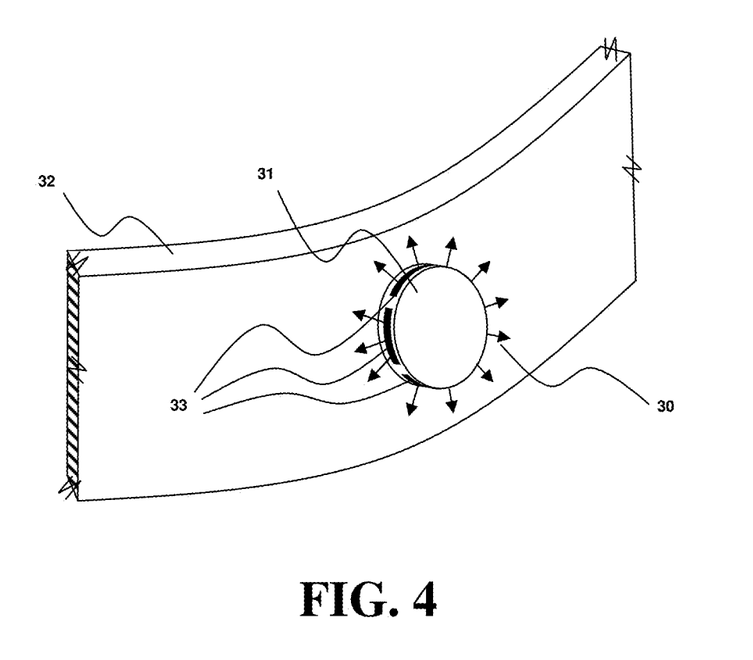
FIG. 4 illustrates a preferred embodiment of an emitter of an airbag inflator.

FIG. 4 illustrates a preferred embodiment of an emitter of an airbag inflator, to achieve better results in distributing the pressure, and avoid excessive impact under the belt. An inflator emitter 31 which may be based on propellant chemical reactions is mounted on the outer side of the belt 32 inside an airbag (airbag is not shown in drawing). The opposite side of the belt faces the user body (not shown in drawing). When the inflator emits gas to the airbag, an impact will be generated in an opposite direction of the gas jet. To avoid strong impact toward user body, the jet emitting directions (marked as arrows 30 in drawing) is designed not towards outside, but in a plane parallel (or almost parallel) to the surface of the belt 32, furthermore, the design makes the jet emitting strength at opposite directions identical or at least nearly identical, so that their impacts cancel each other. To achieve this, the shape of the inflation emitter 31 is preferably symmetric in geometry and the jet emitting holes 33 on the emitter 31 are preferably symmetric about the geometrical center of the emitter 31 in all sectional planes parallel to the mounting surface of belt 32. Besides, jets should be distributed to the emitting holes simultaneously and evenly by design, for example, if the inflator is propellant based, the chemical reaction of propellants needs to take place evenly about the geometrical center of the emitter 31.

Figure 5:
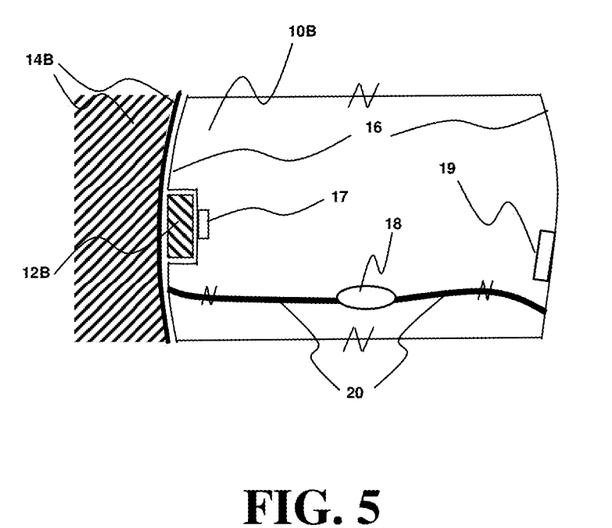
FIG. 5 shows a sectional view of exemplary two-stage inflation embodiments.

In an alternative embodiment, as shown in a partial sectional view in FIG. 5, the airbag 16 may be inflated in two (or more than two) stages. The first stage triggers an inflation emitter 17 mounted on the belt 12B and in turn against user body 14B. During inflation, in order to reduce an impact towards user body 14B under the area of belt 12B, the first stage inflation emitter 17 has relatively small scale, preferably just enough to expand the packed airbag to form its shape. The first stage inflation also pulls additional emitters 18, 19 away from the belt 12B, e.g., pulls the emitter 18 to the middle of the partially inflated airbag 16 by strings (or compartment fabric) 20 tied on both inner and outer sides of the bag 16, or pulls out the emitter 19 that is attached to the outer fabric of the airbag 16; and then, in the second stage of inflation, the emitter 18 in the middle of airbag and/or the emitter 19 attached on the outer fabric of airbag 16 may be ignited, and get the airbag 16 fully inflated. During the second stage of inflation, the emitters 18, 19 are not mounted on the belt 12B, and are preferably designed to emit gas towards opposite directions simultaneously (to avoid the emitter "flies" away by jets). The impact towards user body by the second stage of inflation will be evenly distributed through the entire bag surfaces on the user body side.

Figure 6:
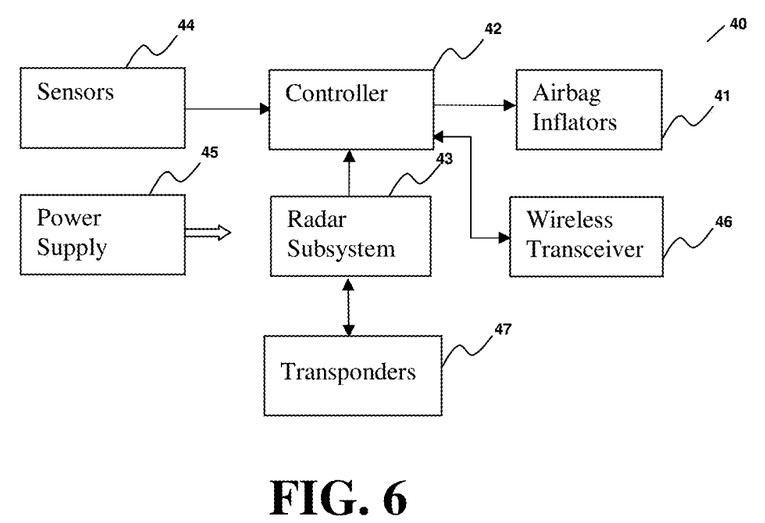
FIG. 6 illustrates a block diagram of an exemplary embodiment of the control system of the wearable airbag device.

FIG. 6 illustrates a block diagram of an exemplary embodiment of the control system 40 of the wearable airbag device. The airbag device is equipped with at least one airbag. In the embodiment shown in FIG. 2, the airbag device is equipped with two airbags, one front bag, and one rear bag. The airbag device may be equipped with multiple airbags, e.g., some airbags to protect the head, some to protect the knee and legs, some to protect the buttock, some to protect the back, some to protect the chest, and some to protect the arms, depending on the protection needs. When more than one airbags are installed, each of them may be controlled to inflate individually, which includes inflating multiple airbags together, one after another, or one airbag alone, depending on the detected risk type by the control system 40. Each individual airbag may be triggered to be inflated by a single inflating device, and may also be triggered to be inflated by more than one inflating devices, depending on the size of the airbag, also depending on other design considerations such as inflating time, acceptable pressure density of the body caused by inflation, and so on. The block of "airbag inflators" 41 in FIG. 6 represents the at least one devices to accept triggering signals (i.e., igniting signals) to activate the inflation of the at least one airbags. An inflator may be designed in separately more than one parts, e.g., an igniter and an emitter, and may also be designed to combine more than one functions in one single part.

The controller 42 is a subsystem that may include at least one microprocessors and signal processors with supporting devices such as memory, clock generation, interfaces to peripheral devices and user, and power management. The controller 42 controls the overall operation of the airbag device (e.g., 1A, 1B in FIG. 1) including the control system 40. Preferably the controller 42 is efficient in energy consumption while providing sufficient processing speed when needed—capable of detecting dangerous conditions and triggering inflation of airbags in the order of milliseconds.

The radar subsystem 43 is responsible for detecting dangerous objects that may hit any protected parts of the body, and send the detected information to the controller 42 for further processing. An object is dangerous to a protected part of the user body if the object and the protected part of the user body are getting closer with a speed higher than a safe speed, and with a distance lower than a safe distance. The radar subsystem 43 preferably is able detect the relative velocity and distance between a surrounding object and the protected portion of the user body in real-time. In a preferred embodiment, the radar subsystem 43 is based on ultrasound signals (for this reason, you may also refer to it as a sonar subsystem). Ultrasound signal is superior to radio signal (electromagnetic signal) for implementing this radar subsystem 43 because many solid objects that may hurt the body does not reflect radio signals, or reflects little. A radio signal based radar may not be able to detect such objects. Ultrasound can be reflected by almost all solid object surfaces. Also, in a preferred embodiment, Doppler effect is used by the radar subsystem to detect the relative velocity between an object and the user body. This gives another reason that ultrasound is superior to radio signal for the radar subsystem 43, because the radio signal propagates at very high speed, relative movements of a surrounding object in a regular user's daily life only cause very small amount of Doppler shift, but ultrasound has much lower propagation speed than radio signals, the Doppler shift would be much more significant, and easier to detect. Preferably the radar subsystem is implemented to be able to detect and measure both relative velocity and distance, and optionally is further able to detect and measure acceleration/deceleration.

The airbag devices may further include various sensors 44 deployed at various positions of the airbag device (e.g., 1A, 1B in FIG. 1) and/or various positions on the user body (not shown in drawings) that are coupled with the controller 42, such as accelerometers (gravimeters), gyro sensors (gyroscope sensors), muscle electrical potential sensors, pressure sensors, microphone, infrared and image sensors, cameras, etc. In one embodiment, the sensors are used to detect the user mode of activity, sometimes referred to as posture mode detection. For example, when detected that a user is sitting (usually this posture has relatively low risk), all devices 40 can enter a mode of operation that reduces energy consumption, to increase battery life of the airbag device. This energy saving mode can be achieved, for example, by reducing the clock rate of the processors in the controller 42, or by periodically putting the processors and devices in an energy saving "sleep" mode. Detecting the user is walking smoothly, for example, the controller 42 may decide to change the mode of operation to a moderate energy consumption rate, because the risk level is moderately high. Detecting the user is in a transition of his/her activity, such as from sitting to standing-up, from standing to walking, from walking straight to making a turn, suddenly stopping walking, etc., these transition periods usually have higher risks and the controller may switch the control system devices 40 to a mode providing highest performance with highest energy consumption. In an alternative embodiment, the sensors provide information for the controller 42 for making a decision of airbag inflation in addition to or jointly with the information provided by the radar subsystem, to increase the level of confidence and reduce false alarms and/or missed detections of dangerous conditions. For example, when a user falls down, accelerometers and/or gyro sensors deployed at upper user body may provide information to the controller to detect the falling condition either solely based on the sensor information, or jointly with radar detected information; while falling, a user would commonly feel nervous and his/her arms may try to reach the ground to support his/her body, muscle electrical potential sensors may detect such user action and provide the detected information to the controller 42 for a decision of airbag inflation. When a pressure sensor embedded in shoes detecting a foot is on floor but a microphone or image or infrared sensor on the shoe detects the foot is still moving (through frictional noise and/or moving images), it is an indication of slipping, the information can be fed to the controller 42 for decision making of airbag inflation. Cameras may record situations through still images and/or videos during events of the airbag inflations. Some sensors may also be used by a 3D body posture determination method that will be described in detail hereinafter.

The power supply unit 45 is responsible for providing power to all subsystems of the control system 40. In a preferred embodiment the power supply unit supports two sets of independent detachable batteries (not shown), and either of the two sets of batteries is able to support the full operation of the airbag control system 40. Preferably the batteries are hot swappable, i.e., any one of the batteries can be replaced while the other battery is automatically on duty without affecting the functionality of the airbag device. The power supply unit will control the use of the two sets of batteries smartly and providing indication which battery needs to be replaced, e.g., for charging offline. When a user is by mistake attempting to replace a wrong battery that is currently powering the airbag device while the other one is depleted, preferably the active battery is automatically locked and not detachable by user.

The control system 40 of the airbag device may further include a wireless transceiver subsystem 46 that is used to report incidents of airbag inflations. The reports may be received by a service center to dispatch service staff to the user in the event of an airbag inflation. Through the wireless transceiver 46, service staff may also speak to the user and/or surrounding people at the user's location to provide guidance to handle situations in an airbag inflation event. Event logging data may also be transmitted to service center through the wireless transceiver 46. Software upgrades may also be downloaded onto the control system 40 through the wireless transceiver 46. Besides, some sensors (in the block 44) may also be coupled to the controller 42 via wireless transceiver 46. The block of wireless transceiver may including more than one wireless air interface technologies, and may also further include global positioning satellite receivers (GPS, GLONASS, Beidou, Galileo and the like) for obtaining user location information.

The control system 40 of the airbag device may further include a number of transponders 47 placed at various locations on the user body, for detecting a falling condition of the user. This feature is explained in detail hereinafter with FIG. 9.

Figure 7:
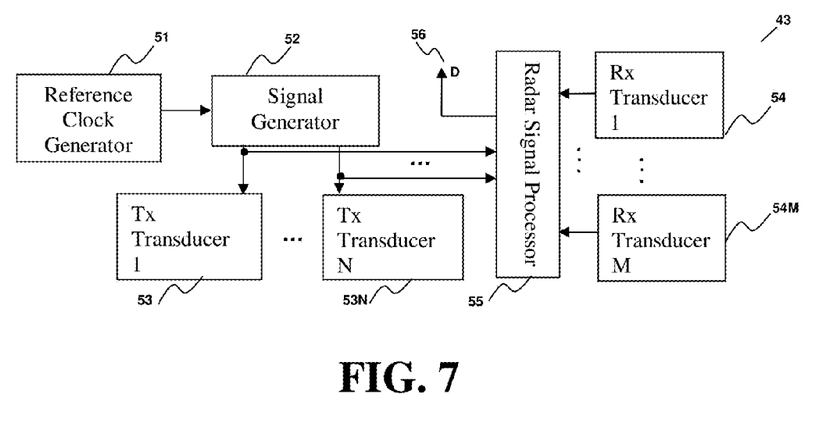
FIG. 7 is an exemplary embodiment of the radar subsystem presented in a more detailed functional block diagram.

FIG. 7 is an exemplary embodiment of the radar subsystem 43 presented in a more detailed functional block diagram. In order to detect dangerous conditions around all protected parts of user body, such as head, shoulders, back, chest, front and rear sides of buttock, knee and thigh, the radar subsystem may deploy a plurality of radars, and they shall coexist without interfering with one another. To achieve this, the radars use a common reference clock generated by a reference clock generator 51. In the exemplary embodiment, the radar subsystem generate N transmitted signals by a signal generator 52, and they are fed to N transmit (Tx) transducers, namely, "Tx transducer 1" 53, . . . , "Tx transducer N" 53N. Since using a common clock, the N signals are synchronized with each other. Further, in the exemplary embodiment, M receiving (Rx) transducers are deployed at various parts of the user body (to be detailed hereinafter), they are, respectively, "Rx transducer 1" 54, . . . , "Rx transducer M" 54M. All the M received signals as well as the N transmitted signals are fed to a radar signal processor 55 for processing, detecting and predicting whether there exist a dangerous object to hit any protected parts of the user body shortly, i.e., relative velocity towards user body higher than a safe threshold and distance shorter than a safe threshold. The velocity threshold is determined by how much momentum a body can bear with, when being hit. Given a "reaction time" (for detection and airbag inflation plus some guard time), the distance threshold may be determined by the detected relative velocity multiplied by the reaction time. Alternatively, computing the "time to hit" as the detected distance divided by the detected relative velocity, and use it as a measure to compare with a safe time threshold. The overall processing may be partially accomplished by the controller 42 (not shown), and the radar signal processor 55 sends its (partially) processed results to the controller 42 by output D 56, and then the controller 42 makes the final decision to inflate selected airbags.

Figure 8:
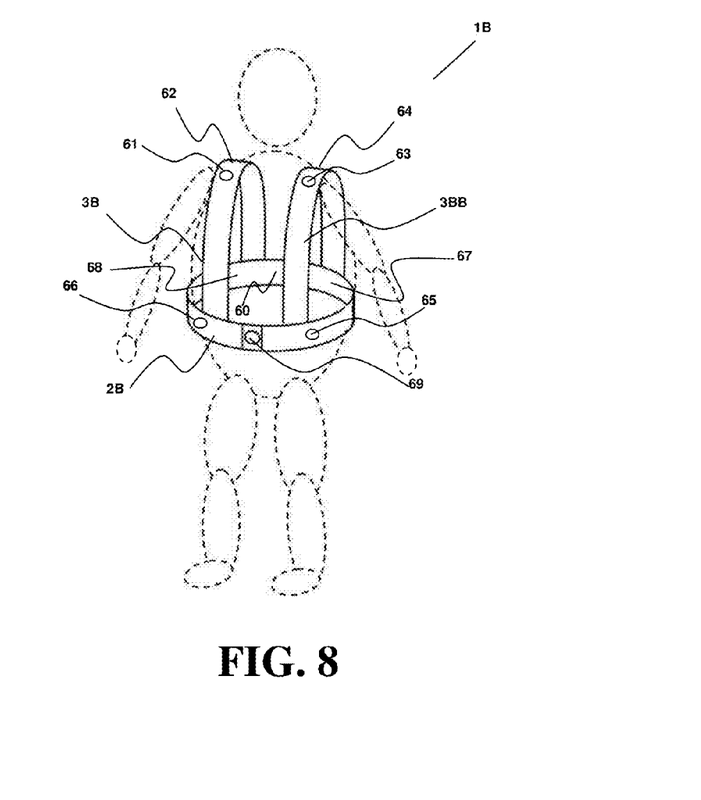
FIG. 8 is an exemplary deployment of the radar transducers for one of the embodiments presented in FIG. 1.

FIG. 8 is an exemplary deployment of the radar transducers for one of the embodiments presented in FIG. 1. In order to reliably detect dangerous objects towards the head, shoulders and upper trunk of the user, preferably four Rx transducers are to be deployed, at front and rear sides of the right and left shoulder belts 3B, 3BB, marked as 61, 62, 63, 64. In order to reliably detect any dangerous objects towards the middle and lower parts of trunk and buttock, knee and thigh, another four Rx transducers are preferably to be deployed, at front left and right sides and rear left and right sides of the waist belt 2B, marked as 65, 66, 67, and 68. The four front Rx transducers 61, 63, 65, 66, may share a single Tx transducer source emitted at a preferred position marked as 69, around the front center of the waist belt 2B. The four rear Rx transducers 62, 64, 67, 68 may share a single Tx transducer source emitted at a preferred position marked as 60, around the rear center of the waist belt 2B.

People skilled in the art would understand that, not only the N radars wearing by the same user (in the example of FIG. 8, N is 8), but also radars on surrounding people who wear similar airbag devices need to avoid interference with one another. Besides, in nature there may exist some sources producing sound in ultrasound frequency. To avoid interference, preferably the signal generator 52 produces radar signals using frequency hopping technique that hops the transmitting signal in frequency by random or pseudorandom sequences. People skilled in the art would also understand that, comparing with conventional radar or sonar for military or navigation purposes, the radar system 43 for wearable airbag control does not need to have sharp beam for detecting object angles in space.

Falling is a dangerous condition that causes a lot of bodily injuries. Accurately detecting falling of a user body will provide high confidence in making airbag inflation decisions. In static condition, falling happens when the gravity vector from center of mass of a human body is pointing outside the supporting base of the body, usually the outer contour of the two feet when standing. The direction of the gravity can be obtained from 3-dimensional accelerometers (gravimeters), preferably by averaging over readings from more than one accelerometers. These accelerometers are preferably mounted on the waist belt in the front and back sides respectively. A human body's center of mass can be calculated by segmentation method, and since the body posture is changing over time, accurately computing the relative positions of the body segments is the key for the center of mass calculation and for the supporting base calculation.

Figure 9:
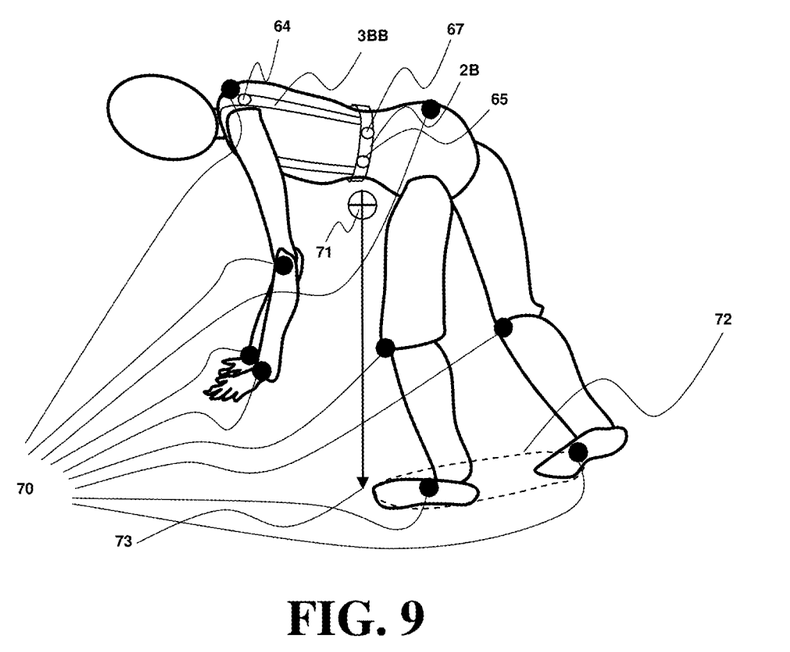
FIG. 9 illustrates a method of 3-dimensional (3D) body posture determination using ultrasound trilateration.

FIG. 9 illustrates a method of 3-dimensional (3D) body posture determination using ultrasound trilateration. In the abstracted diagram, a person wears an airbag device with waist belt 2B and shoulder belts (one is visible as marked 3BB). On the airbag device, a plurality of Rx ultrasound radar transducers are mounted. For example, in the embodiment of FIG. 8, eight Rx transducers were recommended. In the drawing three Rx transducers are visible and they are marked as 65, 67, 64. For purpose of 3D body posture determination, using all these eight Rx transducers is good for performance, but not absolutely necessary. Using the four on the waist belt will work. In the figure, it also shows a number "transponder" devices 70 that are placed on selected important points of body segments to mark the shape of the body posture in 3D. These transponder devices are active "echoers" which receive signals from a designated Tx transducer of ultrasound radar (e.g. 69 in FIG. 8, not shown in FIG. 9), identify a designed time mark in the received signal, and then transmit out a signal with a new time marker having a predetermined (or calibrated known) delay from its received time marker. This way, by measuring the time mark delays received by the plurality of Rx transducers (e.g., 65, 67, 64 and others not shown in drawing), a processor in the controller 42 (not shown in FIG. 9) is able to calculate the positions of the individual transponder devices 70 in 3D using trilateration techniques, and obtain the 3D posture shape of the body segments relative to the transducers.

Through the 3D posture shape and estimated weights of body segments, the center of mass position 71 of the body can be calculated. In this example, the center of mass 71 is outside of the body. Also, the supporting base footprint 72 can also be obtained, as denoted in dashed line. If the projected point on ground 73 of the gravity vector from the body center of mass 71 is significantly outside the supporting base footprint 72, the user body is determined to be falling (out of balance); if the projected point 73 is steadily inside the contour of the supporting base footprint 72, the user body is in balance; if the projected point 73 is close to the contour of the supporting base footprint 72, the user body's balance condition is marginal and may be risky. Note that a transition to sitting is a special "falling" condition that needs to be detected and treated separately. With radar and sensors as well as the method described hereinabove, people skilled in the art will be able to handle it, and thus will not be discussed in detail.

The time mark in the ultrasound radar signal can be implemented in a number of ways, e.g., a transition edge of frequency hopping, a pulse edge modulated onto the ultrasound signal, a designated code sequence, etc. In a preferred embodiment, the transition edge of frequency hopping is used.

Preferably the transponder devices are made small in size, for example as little as or smaller than a button, so that they can be easily attached on clothing without causing any inconvenience.

In using trilateration techniques, constraint conditions (such as the distance between two transponders attached on a single rigid body segment is fixed and known) and over determination using extra measurements (such as extra measurements from more than necessary transducers) may be used to improve accuracy of the posture determination. Such techniques are well known to ones skilled in the art of GPS positioning, and will not be described in detail.

The terminology of "echo" is used in a broad sense. It does not necessarily mean transmit back a signal identical to its received signal. The echoed signal may be different, such as different in frequency, or even different in nature (such as using ultrasound to echo a time mark received in radio signal, etc.). Alternative embodiments are possible, for example, embodiment 1: using ultrasound for both downlink (from radar Tx transducer to transponders) and uplink (from transponders to radar Rx transducers); embodiment 2: use radio for downlink (from a radio transceiver to transponders) and use ultrasound for uplink (from transponders to radar Rx transducers); embodiment 3: use ultrasound for downlink (from 3 or more radar Tx transducers to transponders) and radio as uplink (from transponders to a radio transceiver). In principle all these three embodiments work, but complexity differs, some needs more complicated transponders, some needs more complicated math calculation.

In alternative embodiments, the airbag device may be embedded in a garment such as a vest, a jacket or a coat. Such embodiments are suitable for mild and cold environment conditions other than summer outdoor environment.

The inflators may also use technologies other than propellant based chemical reactions, such as compressed air.

Certain terms are used to refer to particular components. As one skilled in the art will appreciate, people may refer to a component by different names. It is not intended to distinguish between components that differ in name but not in function. For example, in the specification and claims, the terminologies "radar" and "sonar" are used, to refer to detecting and ranging devices based on reflected wave from objects, where the wave used is preferably ultrasound, i.e., to refer to an ultrasonic motion/proximity sensor; the terminology "airbag" may be referred to as "airbag cushion" or "air cushion". The word "hit" in the specification and claims always appears as "an object hits the body", in fact, what matters is they hit each other. In real world it may be "the body hits an object", e.g., falling is that the body hits the ground. It should be understood that throughout this application, "A hits B" always means A and B hits each other without distinguishing subject and object.

The terms "including" and "comprising" are used in an open-ended fashion, and thus should be interpreted to mean "including, but not limited to". The terms "example" and "exemplary" are used simply to identify instances for illustrative purposes and should not be interpreted as limiting the scope of the invention to the stated instances.

Also, the term "couple" in any form is intended to mean either a direct or indirect connection through other devices and connections.

It should be understood that various modifications can be made to the embodiments described and illustrated herein, without departing from the invention, the scope of which is defined in the appended claims.

I claim:

1. An airbag device wearable on a user body for preventing bodily injury of the user, comprising:
    at least one inflatable airbag, mounted on the airbag device for absorbing energy when an object hits the body of the user;
    at least one airbag inflator, for accepting an igniting signal to inflate the at least one inflatable airbag;
    at least one sensor of gravity, placed at predetermined at least one location on the airbag device;
    a plurality of transponders, adapted to be placed at a plurality of distinct locations on the user body and configured to transmit, from each of the plurality of transponders, a time mark signal;
    a plurality of receiving devices, placed at a plurality of distinct locations on the airbag device, for receiving the time mark signals from each of the transponders; and
    a controller, coupled with the at least one airbag inflator, the at least one sensor of gravity, and the plurality of receiving devices, whereby the controller is operable to
        determine a status indicating whether the user is falling based, at last in part, on a timing of the time mark signals received by the plurality of receiving devices, and a direction of gravity measured by the sensor of gravity,
        make decisions of airbag inflation based, at least in part, on the determined status of falling, and
        send, upon positive decision of airbag inflation, the igniting signal to the at least one airbag inflator.

2. The airbag device of claim 1 further including at least one additional sensor, placed at predetermined at least one location on the airbag device or on the body of the user, coupled with the controller, for collecting information for controlling the airbag device.

3. The airbag device of claim 2 further including at least one wireless transceiver for at least one of:
    reporting an airbag inflating incident to at least one predetermined terminal device;
    providing communication means between service staff and the user or a person at the user's location;
    sending event log data to a service center;
    transferring data between the controller and at least one of the sensors;
    transferring signaling between the controller and at least one of the sensors;
    transferring signaling between the controller and the receiving devices;
    transmitting a first time mark signal to the plurality of transponders;
    downloading software upgrades onto the airbag device;
    communicating with cellular basestations for location determination; and
    receiving global positioning satellite signals for location determination.

4. The airbag device of claim 2, wherein said at least one additional sensor includes at least one of:
    at least one accelerometer;
    at least one gravimeter;
    at least one gyro sensor;
    at least one muscle electrical potential sensor;
    at least one pressure sensor;
    at least one microphone;
    at least one infrared sensor;
    at least one image sensor; and
    at least one camera.

5. The airbag device of claim 4, wherein the controller is operable to determine a status indicating whether or not the user is slipping, based on information reported by at least one sensors placed on shoes, out of the at least one additional sensor, and to determine whether or not to inflate the at least one airbag based, at least in part, on the determined status of slipping.

6. The airbag device of claim 4, wherein the controller is operable to determine an activity mode of the user, and further determine a mode of operation of the airbag device, based on the determined activity mode of the user.

7. The airbag device of claim 1, wherein said at least one airbag inflator includes a gas emitter mounted on the airbag device that, when inflating the airbag, performs at least one of:
   emitting gas simultaneously in at least two directions opposite to each other;
   emitting gas simultaneously in at least two directions nearly opposite to each other;
   emitting gas in directions perpendicular to a direction pointing towards outside from a nearest portion of the user body; and
   emitting gas in directions nearly perpendicular to a direction pointing towards outside from a nearest portion of the user body.

8. The airbag device of claim 1, wherein said at least one airbag inflator inflates the airbag in at least two stages, wherein
   the first stage of inflation is performed by a gas emitter firmly mounted on the airbag device; and
   the at least one stage after the first stage of inflation is performed by at least one gas emitter that, while emitting gas, is located inside the airbag and not firmly mounted on the airbag device.

9. The airbag device of claim 1 further including at least one transmitting device, for transmitting at least one of an ultrasound signal, a radio signal and an optical signal.

10. The airbag device of claim 9 wherein the at least one transmitting device is configurable to operate as at least one sonar transmitter, and the plurality of receiving devices are configurable to operate as sonar receivers.

11. The airbag device of claim 10, wherein the sonar receivers makes use of Doppler effect.

12. The airbag device of claim 10, wherein the at least one sonar transmitter transmits ultrasound signals with frequency hopping.

13. The airbag device of claim 10, wherein the controller is further operable to determine whether or not to inflate the at least one airbag based, at least in part, on a detected velocity and a distance of a surrounding object towards the user reported by the sonar receivers.

14. The airbag device of claim 9 wherein the least one transmitting device is configurable to transmit a first time mark signal.

15. The airbag device of claim 14 wherein the transponders transmit the time mark signal in response to the first time mark signal.

16. The airbag device of claim 1, wherein the controller is further operable to determine at least one of:
   relative positions of segments of the user body in 3-dimensions, based on the measured timing of the time mark signals from at least three of the plurality of receiving devices;
   a relative position of center of mass of the user body, based on relative positions and weights of segments of the user body;
   a status indicating the user is sitting or standing;
   a relative position of supporting base footprint, based on relative positions of feet when determined standing, and based on relative positions of feet and buttock when determined sitting;
   a direction of gravity; and
   a status indicating whether or not the user is falling, based on the determined relative position of center of mass of the user body, the determined relative position of supporting base footprint, and the direction of gravity.

17. A personal airbag system for preventing bodily injuries of a user, comprising:
   at least one inflatable airbag, each associated with a protection area of the user body;
   at least one airbag inflator, each associated with one of the at least one airbag, and in turn, associated with its protection area;
   at least one sonar transmitter and at least one sonar receiver, each said sonar receiver associated with at least one protection area of the at least one airbag, for detecting a velocity of an object towards and relative to the at least one associated protection area;
   at least one sensor placed on shoes of the user, for detecting a slipping condition on at least one foot;
   a controller with a storage medium, coupled with the at least one airbag inflator, the at least one sonar transmitter, the at least one sonar receiver, and the at least one sensor;
   computer instructions stored in the storage medium; and
   the computer instructions being executable by the controller for:
   determining a slipping condition on at least one foot based on information reported by the at least one sensor placed on shoes;
   determining a falling condition based, at least in part, on the slipping condition;
   determining, for each of the at least one sonar receiver, whether the detected velocity exceeds a preprogrammed threshold; and
   if determined positive, causing each of the at least one airbag inflator associated with the protected area that the sonar receiver in question is associated with, to inflate.

* * * * *